United States Patent [19]

Ho et al.

[11] Patent Number: 4,552,891

[45] Date of Patent: Nov. 12, 1985

[54] BENZOTHIOPHENE DERIVATIVES

[75] Inventors: Peter P. K. Ho, Carmel; Quentin F. Soper, Indianapolis, both of Ind.

[73] Assignee: Eli Lilly and Company, Indianapolis, Ind.

[21] Appl. No.: 531,802

[22] Filed: Sep. 13, 1983

[51] Int. Cl.$^4$ .............................................. A61K 31/38
[52] U.S. Cl. .................................................... 514/443
[58] Field of Search ......................... 424/275; 514/443

[56] References Cited

U.S. PATENT DOCUMENTS 3,751,430 8/1973 Libis et al. ........................... 424/275
4,101,668 7/1978 Samour et al. ...................... 424/275

OTHER PUBLICATIONS

Tetrahedron, 25 (14), 2781 (1969).
J. Chem. Soc., 1314 (1953).
J. Org. Chem., 26, 359 (1961).
J. Org. Chem., 26, 1326 (1961).
J. Org. Chem., 21, 39 (1956).
Aust. J. Chem., 32 (4), 833 (1979).
J. Org. Chem., 26, 1327 (1961).
J. Org. Chem., 37 (21), 3224 (1972).
J. Het. Chem., 12 (5), 889 (1975).
Acta Pharm. Suec., 15, 368 (1978).

Primary Examiner—Leonard Schenkman
Assistant Examiner—Joseph A. Lipovsky
Attorney, Agent, or Firm—Charles W. Ashbrook; Arthur R. Whale

[57] ABSTRACT

This invention provides for pharmaceutical formulations of certain benzothiophene derivatives and a method of using the derivatives or formulations for the treatment of asthma.

10 Claims, No Drawings

BENZOTHIOPHENE DERIVATIVES

BACKGROUND OF THE INVENTION

Recent studies have confirmed that theophylline is probably the most effective bronchodilator for the treatment of asthma that can be administered parenterally and orally. Unfortunately, the therapeutic range for theophylline is fairly narrow and its toxic effects stem largely from its action on the central nervous system, cardiovascular system, and gastrointestinal tract. It has been suggested that these undesirable pharmacological activities as well as the bronchodilation effect are related to theophylline's ability to competitively inhibit phosphodiesterase (PDE), which is an enzyme that degrades cyclic AMP. Thus, it is desirable to discover selective inhibitors of cyclic AMP phosphodiesterase which possess a beneficial bronchodilation effect but lack most of the adverse reactions of theophylline.

This invention relates to the discovery that certain 5,6-disubstituted-benzothiophene-2-carboxylic acids are potent phosphodiesterase inhibitors and bronchodilators. 5,6-Dimethoxybenzothiophene-2-carboxylic acid was first prepared by Bew and Clemo, *J. Chem. Soc.*, 1314 (1953) and later by Campaigne and Kreighbaum (*J. Org. Chem.*, 26, 359 (1961)). See also *Tetrahedron*, 25 (14), 2781 (1969). In *J. Org. Chem.*, 26, 1327 (1961), Campaigne teaches that certain amide derivatives were found to possess analgesic and diuretic activity. Campaigne also teaches 5,6-diethoxybenzothiophene-2-carboxylic acid (*J. Org. Chem.*, 26, 1326 (1961)) although no pharmaceutical utility is disclosed.

SUMMARY OF THE INVENTION

This invention provides for the use of compounds represented by formula I

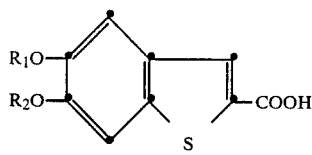

and pharmaceutically acceptable salts thereof wherein each of $R_1$ and $R_2$ is independently hydrogen or $C_1$–$C_7$ alkyl, as agents capable of causing bronchodilation in mammals. More specifically, this invention provides for a method of treating a mammal suffering from or susceptible to asthma, which comprises administering to said mammal an effective amount of a compound of formula I.

According to a further aspect of the present invention there is provided a pharmaceutical formulation which comprises a compound of formula I as described above associated with a pharmaceutically acceptable carrier.

DETAILED DESCRIPTION AND PREFERRED EMBODIMENT

The preferred compounds of this invention are those wherein each of $R_1$ and $R_2$ is independently methyl ethyl, or propyl. Especially preferred is a compound wherein $R_1$ is ethyl. The most preferred compounds are 5,6-diethoxybenzothiophene-2-carboxylic acid and 5-ethoxy-6-propyloxybenzothiophene-2-carboxylic acid and pharmaceutically acceptable salts thereof.

The term "$C_1$–$C_7$ alkyl" refers to straight and branched aliphatic radicals of one to seven carbon atoms such as methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), hexyl, isohexyl (4-methylpentyl, sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 2,2-dimethylpentyl, 3,3-dimethylbutyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, and the like. Straight chain radicals are preferred and methyl, propyl, and especially ethyl are most preferred.

The pharmaceutically acceptable base addition salts of this invention include salts derived from inorganic bases, such as ammonium and alkali and alkaline earth metal hydroxides, carbonates, bicarbonates, and the like, as well as salts derived from non-toxic basic organic amines, such as aliphatic and aromatic amines, aliphatic diamines, hydroxy alkylamines, and the like. Such bases useful in preparing the salts of this invention thus include sodium hydroxide, sodium acetate, ammonium hydroxide, potassium carbonate, sodium bicarbonate, calcium hydroxide, methyl amine, diethyl amine, ethylenediamine, cyclohexylamine, ethanolamine, and the like. The potassium and sodium salt forms are particularly preferred.

The compounds of formula I are prepared by methods known in the art. These include the cyclization of a 3,4-dialkoxyphenylpropiolic acid chloride with thionyl chloride (Bonnin, et al., *Aust. J. Chem.*, 32 (4), 833 (1979), the reaction of a 4,5-dialkoxy-2-nitrobenzaldehyde with methyl thioglycolate followed by hydrolysis of the resulting methyl esters of compounds I (Beck, *J. Org. Chem.*, 37 (21), 3224 (1972), the condensation of a 4,5-alkoxy-2-mercaptobenzaldehyde with a haloacetic acid followed by cyclization (Bew and Clemo, *J. Chem. Soc.*, 1314 (1953)), or preferably the cyclization of a β-(3,4-disubstituted-phenyl)-α-mercaptoacrylic acid (Campaigne and Kreighbaum, *J. Org. Chem.*, 26, 359 (1961); id., 26, 1326 (1961); Chakrabarti, et al., *Tetrahedron*, 25 (14), 2781 (1969)).

In addition, compounds of formula I can also be prepared from other compounds of formula I. A dialkoxy compound of formula I can be first esterified by methods known in the art and then mono-dealkylated to provide 5-alkoxy-6-hydroxy- and/or 5-hydroxy-6-alkoxy-derivatives or di-dealkylated to provide the corresponding 5,6-dihydroxy compound after hydrolysis of the ester group by any of the usual methods. These dealkylations can be performed using methods known in the art such as boron tribromide in ethylene dichloride, a mixture of methanesulfonic acid/methionine, or ethanethiol/aluminum chloride in ethylene chloride. The resulting hydroxy or dihydroxy ester intermediates can be hydrolyzed to the carboxylic acid compounds of this invention and can also be converted to other compounds of this invention by mono- or di-alkylation in the usual way with the appropriate alkyl halide preferably in a nonreactive solvent and an acid scavenger, followed by hydrolysis of the ester group.

The compounds may be administered by various routes including the oral, rectal, transdermal, subcutaneous, intravenous, intramuscular, inhalation, or intranasal routes, being usually employed in the form of a pharmaceutical composition. Such compositions are prepared in a manner well known in the pharmaceutical art and comprise at least one active compound. Accordingly, the invention includes a pharmaceutical composition comprising as active ingredient a compound of Formula I or a pharmaceutically acceptable salt thereof associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

Preferably the compositions are formulated in a unit dosage form, each dosage containing from about 5 to 500 mg. (from about 5 to 50 mg. in the case of parenteral or inhalation administration, and from about 25 to 500 mg. in the case of oral or rectal administration) of a compound of formula I. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg./kg. In the treatment of adult humans, the range of about 1 to 50 mg./kg., in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

Preferred pharmaceutical forms of the present invention are capsules, tablets, suppositories, injectable solutions, creams and ointments. Especially preferred are formulations for inhalation or insufflation application, such as an aerosol, and for oral ingestion.

The following examples further illustrate the preparation of the starting materials, intermediates, and compounds used in this invention. The examples are illustrative only and are not intended to limit the scope of the invention in any way.

EXAMPLE 1

5,6-Diethoxybenzothiophene-2-carboxylic acid

A. Preparation of 5-(3,4-diethoxybenzylidene)rhodanine

A solution of 10.0 g. of 3,4-diethoxybenzaldehyde, 6.86 g. of rhodanine, and 14.5 g. of fused sodium acetate in 70 ml. of acetic acid was heated to reflux for one hour. The hot mixture was poured into one liter of water with stirring. The resulting precipitate was collected by filtration and dried. Recrystallization from ethanol provided 10.22 g. of the subtitle intermediate.

B. Preparation of β-(3,4-diethoxyphenyl)-α-mercaptoacrylic acid

A solution of 33.0 g. of 5-(3,4-diethoxybenzylidene)rhodanine and 23.4 g. of sodium hydroxide in 148 ml. of water was heated to 70° C. for 30 minutes. The solution was cooled and filtered and the filtrate was acidified by pouring into excess cold 10% hydrochloric acid. The precipitate was collected by filtration affording 25 g. of the desired subtitle intermediate which was used without further purification.

C. Preparation of 5,6-diethoxybenzothiophene-2-carboxylic acid

Two grams of β-(3,4-diethoxyphenyl)-α-mercaptoacrylic acid were dissolved in 68.5 ml. of dioxane. To the solution were added 2.74 g. of iodine. The solution was heated at 60°–70° C. for 22 hours. The reaction was then poured into 550 ml. of water, decolorized with 11.0 g. of sodium bisulfite, and stirred vigorously for several minutes. The crude product was collected by filtration and dissolved in approximately 15 ml. of a warm 10% sodium hydroxide solution. The alkaline solution was treated with decolorizing carbon and filtered. The solution was allowed to stand at refrigerator temperature overnight. The resulting pink crystals were collected and dissolved in water. Dilute hydrochloric acid was added and the resulting precipitate was collected to give 0.59 g. of the desired title product. Two recrystallizations from 95% ethanol gave white needles, m.p. 243°–245° C.

Analysis: $C_{13}H_{14}O_4S$; Calc.: C, 58.63; H, 5.30; S, 12.04; Found: C, 58.84; H, 5.03; S, 12.05.

EXAMPLES 2–9

Following the general procedure of Example 1, the following benzothiophene-2-carboxylic acids were prepared from rhodanine and the corresponding benzaldehyde derivatives. Yields are expressed as the percent molar yield from the benzaldehyde.

2. 5-Methoxy-6-ethoxybenzothiophene-2-carboxylic acid, m.p. 236°–238° C., 12% yield.

Analysis: $C_{12}H_{12}O_4S$; Calc.: C, 57.13; H, 4.79; S, 12.71; Found: C, 57.22; H, 5.05; S, 12.45.

3. 5-Methoxy-6-butyloxybenzothiophene-2-carboxylic acid, 10.5% yield. Mass spectrum: M+ = 280.

Analysis: $C_{14}H_{16}O_4S$; Calc.: C, 59.98; H, 5.75; S, 11.44; Found: C, 60.10; H, 5.87; S, 11.22.

4. 5-Methoxy-6-hexyloxybenzothiophene-2-carboxylic acid, m.p. 165°–166° C., 13% yield.

Analysis: $C_{16}H_{20}O_4S$; Calc.: C, 62.31; H, 6.54; S, 10.40; Found: C, 62.51; H, 6.28; S, 10.13.

5. 5-Methoxy-6-heptyloxybenzothiophene-2-carboxylic acid, m.p. 163°–164° C., 9.4% yield.
Analysis: $C_{17}H_{22}O_4S$; Calc.: C, 63.33; H, 6.88; Found: C, 63.11; H, 6.96.

6. 5,6-Dihydroxybenzothiophene-2-carboxylic acid, 5.5% yield. Mass spectrum: $M^+ = 210$.
Analysis: $C_9H_6O_4S$; Calc.: C, 51.43; H, 2.88; S, 15.25; Found: C, 51.68; H, 3.11; S, 15.01.

7. 5-Hydroxy-6-methoxybenzothiophene-2-carboxylic acid, m.p. 190° C. (decomposition), 3.4% yield. Mass spectrum: $M^+ = 224$.
Analysis: $C_{10}H_8O_4S$; Calc.: C, 53.56; H, 3.60; S, 14.30; Found: C, 53.79; H, 3.65; S, 14.09.

8. 5-Ethoxy-6-hydroxybenzothiophene-2-carboxylic acid, m.p. 210.5°–211° C., 6% yield.
Analysis: $C_{11}H_{10}O_4S$; Calc.: C, 55.45; H, 4.23; Found: C, 55.47; H, 4.36.

9. 5,6-Dimethoxybenzothiophene-2-carboxylic acid, m.p. 257°–258° C., 7% yield.
Analysis: $C_{11}H_{10}O_4S$; Calc.: C, 55.45; H, 4.23; S, 13.46; Found: C, 55.72; H, 4.25; S, 12.72.

EXAMPLE 10

5-Ethoxy-6-propyloxybenzothiophene-2-carboxylic acid

A. Preparation of methyl 5-ethoxy-6-hydroxybenzothiophene-2-carboxylate

A solution of 0.71 g. of 5-ethoxy-6-hydroxybenzothiophene-2-carboxylic acid, 0.29 g. of methanol, and a catalytic amount of sulfuric acid in methylene chloride was heated to reflux for 48 hours. The solution was diluted with ethyl acetate and was washed first with a 10% aqueous sodium bicarbonate solution and then with water. The organic solution was dried over sodium sulfate and evaporated to dryness providing the desired ester intermediate which was used without further purification.

B. Preparation of methyl 5-ethoxy-6-propyloxybenzothiophene-2-carboxylate

A solution of 0.42 g. of methyl 5-ethoxy-6-hydroxybenzothiophene-2-carboxylate, 0.25 g. of potassium carbonate, a catalytic amount of potassium iodide, and 0.31 g. of propyl iodide in methyl ethyl ketone was heated to reflux for 48 hours. The hot solution was filtered and the filtrate was evaporated in vacuo to provide the desired subtitle intermediate which was used in the subsequent reaction without purification.

C. Preparation of 5-ethoxy-6-propyloxybenzothiophene-2-carboxylic acid

A solution of 0.45 g. of methyl 5-ethoxy-6-propyloxybenzothiophene-2-carboxylate and 0.34 g. of potassium hydroxide in ethanol was heated to reflux for two hours. The solution was poured into water, acidified with hydrochloric acid, and extracted with ethyl acetate. The ethyl acetate layer was extracted with 1N sodium hydroxide. The alkaline solution was acidified with hydrochloric acid and was then extracted with ethyl acetate. The organic extract was dried over sodium sulfate and evaporated in vacuo to provide the desired title product, m.p. 192°–194° C., in an overall molar yield of 36% from 5-ethoxy-6-hydroxybenzothiophene-2-carboxylic acid.
Analysis: $C_{14}H_{16}O_4S$; Calc.: C, 59.98; H, 5.75; Found: C, 59.78; H, 5.99.

EXAMPLES 11–12

Following the general procedure of Example 10, the following compounds were prepared from the corresponding hydroxybenzothiophene-2-carboxylic acid and appropriate alkyl halide. Yields are expressed as the percent molar yield from the hydroxybenzothiophene-2-carboxylic acids.

11. 5-Ethoxy-6-methoxybenzothiophene-2-carboxylic acid, m.p. 233°–234.5° C., 50% yield.
Analysis: $C_{12}H_{12}O_4S$; Calc.: C, 57.13; H, 4.79; Found: C, 56.97; H, 4.81.

12. 5-Propyloxy-6-methoxybenzothiophene-2-carboxylic acid, m.p. 172°–173° C., 50% yield. Mass spectrum: $M^+ = 266$.
Analysis: $C_{13}H_{14}O_4S$; Calc.: C, 58.63; H, 5.30; S, 12.04; Found: C, 57.04; H, 5.05; S, 11.85.

The following formulation examples may employ as active compounds any of the pharmaceutical compounds of the invention.

EXAMPLE 13

Hard gelatin capsules are prepared using the following ingredients:

|  | Quantity (mg./capsule) |
| --- | --- |
| Active compound | 250 |
| Starch | 200 |
| Magnesium stearate | 10 |

The above ingredients are mixed and filled into hard gelatin capsules in 460 mg. quantities.

EXAMPLE 14

A tablet formula is prepared using the ingredients below:

|  | Quantity (mg./tablet) |
| --- | --- |
| Active compound | 250 |
| Cellulose, microcrystalline | 400 |
| Silicon dioxide, fumed | 10 |
| Magnesium stearate | 5 |

The components are blended and compressed to form tablets each weighing 665 mg.

EXAMPLE 15

An aerosol solution is prepared containing the following components:

|  | Weight % |
| --- | --- |
| Active ingredient | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

EXAMPLE 16

Tables each containing 60 mg. of active ingredient are made up as follows:

| | |
|---|---|
| Active ingredient | 60 mg. |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 17

Capsules each containing 80 mg. of medicament are made as follows:

| | |
|---|---|
| Active ingredient | 80 mg. |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 18

Suppositories each containing 225 mg. of active ingredient are made as follows:

| | |
|---|---|
| Active ingredient | 225 mg. |
| Unsaturated or saturated fatty acid glycerides to | 2,000 mg. |

The active ingredient is passed through a No. 60 mesh U.S. sieve and suspended in the fatty acid glycerides previously melted using the minimum heat necessary. The mixture is then poured into a suppository mold of nominal 2 g. capacity and allowed to cool.

EXAMPLE 19

Suspensions each containing 50 mg. of medicament per 5 ml. dose are made as follows:

| | |
|---|---|
| Active ingredient | 50 mg. |
| Sodium carboxymethyl cellulose | 50 mg. |
| Sugar | 1 g. |
| Methyl paraben | 0.05 mg. |
| Propyl paraben | 0.03 mg. |
| Flavor | q.v. |
| Color | q.v. |
| Purified water to | 5 ml. |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

The compounds taught in this invention and their pharmaceutically acceptable salts possess useful pharmaceutical properties. The compounds are useful as inhibitors of the enzyme phosphodiesterase and are also useful in blocking anaphylactic responses and bronchoconstriction. The compounds are therefore useful in treating mammals suffering from or susceptible to asthma. This biological activity was demonstrated in the following test system.

Following the general procedure taught by Andersson, *Brit. J. Pharmacol.*, 69, 467 (1980), mixed sex Hartley strain guinea pigs (250-300 g.) were sensitized to ovalbumin by a single injection of 1 mcg. of ovalbumin mixed with 50 mg. of aluminum hydroxide per animal. These animals were used 21 to 26 days later for aerosol challenge with ovalbumin.

Anaphylaxis was induced by exposure to an aerosol of 10 mg. of ovalbumin per milliliter of water for 10 minutes delivered by a Tri-R venturi nebulizer, particle size 2 to 5 micron diameter, at a delivery rate of 0.4 ml. of solution per minute. The guinea pigs were placed in specially constructed chamber for exposure to the aerosol. The aerosol was introduced from the bottom of the chamber and exhausted at the top. A baffle above the chamber inlet port provided even distribution of the aerosol throughout the chamber. The animals were supported above the inlet on a wire mesh disc. The chamber was under slight negative pressure to enhance the exhaust of the aerosol which was passed through a calcium chloride trap followed by a super-cooled condenser trap.

Groups of five guinea pigs were treated with the compounds of this invention, clinical anti-asthmatic agents, or placebo (vehicle only) two hours prior to the aerosol challenge. All the animals also received 3 mg./kg. pyrillamine orally two hours prior to the aerosol challenge in order to blunt the histamine component of the anaphylaxis. The compounds were administered orally as a suspension in 10% acacia.

Throughout the ten minute period of aerosol challenge, the animals were observed for the symptomology of convulsive cough, convulsive collapse, and death as described by Herxheimer, *J. Physiology*, 117, 251 (1952). The number of animals that responded to the aerosol challenge for each of the above parameters as well as the time for the response to occur were recorded. The data were analyzed by comparing the severity index (the sum of the number of animals that coughed, collapsed, and/or died) between the treated and placebo group of guinea pigs. Thus, the maximum severity index for each group of five guinea pigs is 15. On the average, the severity index for the placebo group was 10-12. The percent inhibition of anaphylaxis was determined by the following formula:

$$\% \text{ inhibition} = \left[1 - \frac{S_d}{S_p}\right] \times 100$$

where $S_d$ is the severity index for the drug treated animals and $S_p$ is the severity index of the placebo treated animals. The results of these experiments are summarized in Table 1.

TABLE 1

| Antigen induced anaphylaxis in guinea pigs | |
|---|---|
| Compound of Example No. | Percent Inhibition* |
| 1 | 93% |
| 2 | 55% |
| 3 | 23% |
| 4 | 18% |
| 5 | 38% |
| 6 | 40% |
| 7 | 63% |
| 8 | 0% |
| 9 | 30% |
| 10 | 90% |
| 11 | 5% |
| 12 | 30% |

*Average of two experiments. Compounds were given orally at a dose of 50 mg./kg.

We claim:

1. A method of treating a mammal suffering from or susceptible to an asthmatic attack, which comprises administering to said mammal an effective amount of a compound of the formula

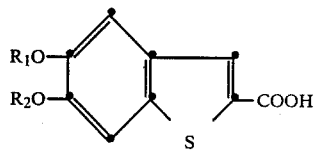

I wherein each of $R_1$ and $R_2$ is independently hydrogen or $C_1$–$C_7$ alkyl, or a pharmaceutically acceptable salt thereof.

2. The method according to claim 1 wherein $R_1$ is ethyl.

3. The method according to claim 2 wherein the compound is 5,6-diethoxybenzothiophene-2-carboxylic acid or a pharmaceutically acceptable salt thereof.

4. The method according to claim 2 wherein the compound is 5-ethoxy-6-propyloxybenzothiophene-2-carboxylic acid or a pharmaceutically acceptable salt thereof.

5. A pharmaceutical formulation in unit dosage form adapted for administration to obtain an antiasthma effect, comprising, per unit dosage, an effective non-toxic amount within the range from about 5 to about 500 mg of a compound of the formula

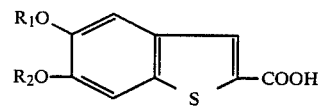

I wherein each of $R_1$ and $R_2$ is independently hydrogen or $C_1$–$C_7$ alkyl, or a pharmaceutically acceptable salt thereof, in association with a pharmaceutically acceptable carrier.

6. A formulation of claim 5 wherein $R_1$ is ethyl.

7. A formulation of claim 6 wherein the compound is 5-ethoxy-6-propyloxybenzothiophene-2-carboxylic acid or a pharmaceutically acceptable salt thereof.

8. A formulation of claim 6 wherein the compound is 5,6-diethoxybenzothiophene-2-carboxylic acid or a pharmaceutically acceptable salt thereof.

9. A formulation of claim 8 which is formulated for inhalation.

10. A formulation of claim 8 which is formulated for oral ingestion.

* * * * *